United States Patent
Demarest et al.

(10) Patent No.: US 7,159,444 B2
(45) Date of Patent: Jan. 9, 2007

(54) COMBUSTIBLE GAS DETECTION SYSTEMS AND METHOD THEREOF

(75) Inventors: Edward Demarest, Bristol, CT (US);
John Koopman, Colchester, CT (US);
Norman Schaefer, Riverton, CT (US);
Andrzej Stanek, Meriden, CT (US);
Iris Shiroma, New Haven, CT (US);
Allan Tomasco, Southington, CT (US);
Elena Stockton, Wallingford, CT (US);
Frano Barbir, Rocky Hill, CT (US);
John Zagaja, East Granby, CT (US);
Thomas Skoczylas, Guilford, CT (US);
Lawrence Moulthrop, Windsor, CT (US)

(73) Assignee: Proton Energy Systems, Inc., Wallingford, CT (US)

( * ) Notice: Subject to any disclaimer, the term of this patent is extended or adjusted under 35 U.S.C. 154(b) by 107 days.

(21) Appl. No.: 10/065,862

(22) Filed: Nov. 26, 2002

(65) Prior Publication Data
US 2004/0099045 A1 May 27, 2004

(51) Int. Cl.
*G01N 27/00* (2006.01)
(52) U.S. Cl. .................. 73/23.2; 73/23.31; 73/31.05; 73/31.07
(58) Field of Classification Search .............. 73/23.2, 73/23.31, 31.05, 31.07
See application file for complete search history.

(56) References Cited

U.S. PATENT DOCUMENTS

| | | | |
|---|---|---|---|
| 4,271,474 A | 6/1981 | Belanger et al. | |
| 5,055,690 A | 10/1991 | Bonne | |
| 5,153,139 A * | 10/1992 | Volz-Thomas et al. | ....... 436/32 |
| 5,334,295 A | 8/1994 | Gallagher et al. | |
| 5,401,470 A | 3/1995 | Poli | |
| 5,578,278 A * | 11/1996 | Fall et al. | .................... 422/234 |
| 5,690,797 A * | 11/1997 | Harada et al. | ........... 204/228.5 |
| 5,707,148 A | 1/1998 | Visser et al. | |
| 6,096,178 A | 8/2000 | Amirav et al. | |
| 6,251,243 B1 | 6/2001 | Lindsay | |
| 6,428,684 B1 | 8/2002 | Warburton | |
| 6,442,994 B1 | 9/2002 | Slater | |
| 6,454,923 B1 | 9/2002 | Dodgson et al. | |
| 6,468,412 B1 | 10/2002 | Bryan et al. | |
| 6,475,651 B1 | 11/2002 | Wilkinson et al. | |
| 6,604,405 B1 | 8/2003 | Whynall et al. | |
| 2002/0110713 A1 | 8/2002 | Reindl et al. | |

FOREIGN PATENT DOCUMENTS

WO    WO-99/17110 A1    4/1999

* cited by examiner

*Primary Examiner*—Daniel S. Larkin
(74) *Attorney, Agent, or Firm*—Dave S. Christensen

(57) ABSTRACT

A system and method are provided for monitoring the levels of combustible gas in a gas stream. The system includes means for controlling the relative humidity of the the gas stream to maintain a humidity level in the performance range of combustible gas sensors. A number techniques are illustrated for achieving the humidity control, including, secondary phase separations, mixing the gas with dry air and adjusting of the gas stream temperature.

9 Claims, 9 Drawing Sheets

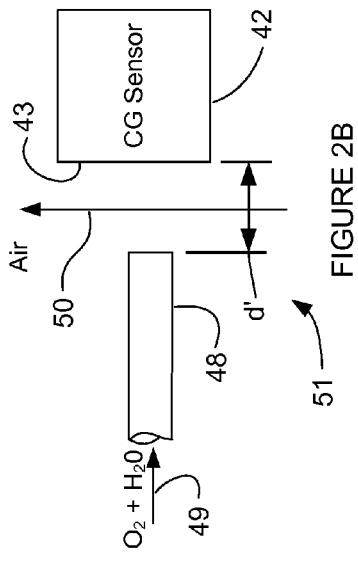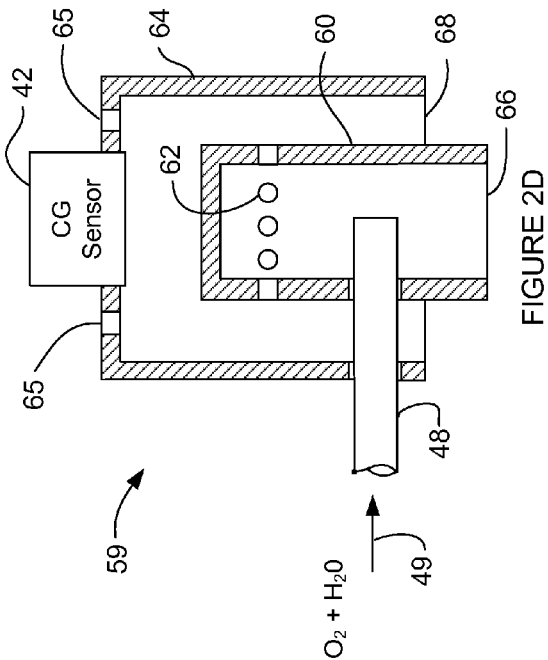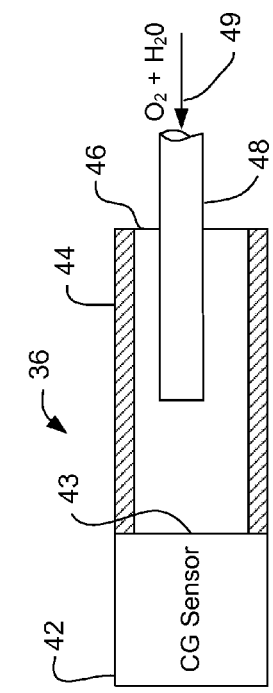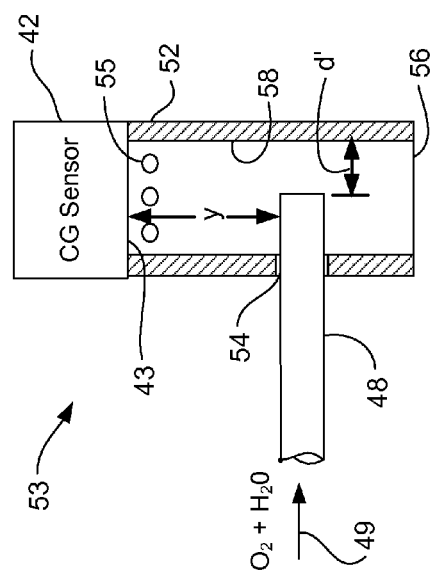
FIGURE 2A
FIGURE 2B
FIGURE 2C
FIGURE 2D

COMBUSTIBLE GAS DETECTION SYSTEMS AND METHOD THEREOF

FIELD OF INVENTION

This disclosure relates generally to the detection of combustible gases, and especially relates to the detection of hydrogen in a vent gas stream.

BRIEF DESCRIPTION OF THE RELATED ART

Hydrogen gas is used and produced in many applications. Since the amount of hydrogen in a gas stream produced by a given process may be an indicator of system efficiency, the systems typically utilize combustible gas sensors to determine the level of hydrogen. An example of a prior art system having an arrangement for monitoring combustible gas is shown in FIG. 1A. The electrochemical system 12 receives water from an external source 14 and passes it through a deionizing bed 16. Once the water has been properly conditioned, it is supplied to an electrochemical cell 18 which disassociates the hydrogen and oxygen.

One example of an electrochemical cell 18 is a proton exchange membrane electrolysis cell which can function as a hydrogen generator by electrolytically decomposing water to produce hydrogen and oxygen gas, and can function as a fuel cell by electrochemically reacting hydrogen with oxygen to generate electricity. Referring to FIG. 1B, which is a partial section of a typical anode feed electrolysis cell 100, conditioned water 102 is fed into cell 100 on the side of an oxygen electrode (anode) 116 to form oxygen gas 104, electrons, and hydrogen ions (protons) 106. The reaction is facilitated by the positive terminal of a power source 120 electrically connected to anode 116 and the negative terminal of power source 120 connected to a hydrogen electrode (cathode) 114. The oxygen gas 104 and a portion of the process water 108 exit cell 100, while protons 106 and water 110 migrate across a proton exchange membrane 118 to cathode 114. At cathode 114, hydrogen gas 112 is formed and removed. Water 110 is also removed from cathode 114.

A typical fuel cell uses the same general configuration as is shown in FIG. 1B. Hydrogen gas is introduced to the hydrogen electrode (the anode in fuel cells), while oxygen, or an oxygen-containing gas, such as air, is introduced to the oxygen electrode (the cathode in fuel cells). Water can also be introduced with the feed gas. The hydrogen gas for fuel cell operation can originate from a pure hydrogen source, hydrocarbon, methanol, or any other hydrogen source that supplies hydrogen at a purity suitable for fuel cell operation (i.e., a purity that does not poison the catalyst or interfere with cell operation). Hydrogen gas electrochemically reacts at the anode to produce protons and electrons, wherein the electrons flow from the anode through an electrically connected external load, and the protons migrate through the membrane to the cathode. At the cathode, the protons and electrons react with oxygen to form water, which additionally includes any feed water that is dragged through the membrane to the cathode. The electrical potential across the anode and the cathode can be exploited to power an external load.

In other embodiments, one or more electrochemical cells can be used within a system to both electrolyze water to produce hydrogen and oxygen, and to produce electricity by converting hydrogen and oxygen back into water as needed. Such systems are commonly referred to as regenerative fuel cell systems.

After the electrochemical cell 18 (FIG. 1A) disassociates the water, oxygen and hydrogen gas exit the cell 18 through conduits 20 and 22, respectively. As mentioned herein above, water entrained in the gas products, water entrained in the gases exits with the oxygen and hydrogen. The hydrogen conduit 22 typically connects with a hydrogen phase separator 24 which extracts most of the water from the gas, with the water exiting the phase separator 24 through a valving arrangement which recycles the water back into the electrochemical cell water feed conduit. Depending on the needs of the application, additional water may be removed from the hydrogen gas by passing through an optional dessicant gas dryer 26 before exiting the process for use in the application.

The oxygen gas stream 20 also enters into a phase separator 28 with a majority of the water separating from the gas stream and dropping to the bottom of the separator 28. As with the hydrogen separator 24, this water is removed via a valving arrangement 30 and recycled into the electrochemical cell water feed conduit. The separated hydrogen gas exits the phase separator 28 via a conduit 32 to exit the process. Since it is desirable to monitor for the presence of hydrogen gas in the oxygen gas stream, the oxygen phase separator 28 includes a second outlet 34 which provides a sample gas stream through an orifice 40 to a combustible gas sensor 36. A gas dryer 38, such as a NAFION tube dryer, is usually placed inline between the phase separator 28 and the sensor 36 to remove water still entrained in the gas. Unfortunately, since the gas stream can still have a relative humidity greater than 95%, this high relative humidity results in lower monitoring performance than is desired.

Accordingly, what is needed in the art is a system for monitoring combustible gas levels in a gas stream that reduces or eliminates the effects of relative humidity on combustible gas sensing.

SUMMARY OF INVENTION

Disclosed herein are systems and methods for monitoring combustible gas levels in a gas stream. In an exemplary embodiment of a system for monitoring combustible gas that comprises: a first phase separator having first outlet; a second phase separator having an inlet and at least one outlet having a opening therefrom, said second separator inlet being fluidly connected to said first separator outlet; and a first combustible gas sensor adjacent said second separator outlet, said first sensor being spaced a predetermined distance from said second separator outlet opening.

Another embodiment includes a electrochemical system that comprises: an electrochemical cell stack having an oxygen outlet; a first phase separator having an inlet and at least one outlet, said inlet being connected to said cell stack oxygen outlet; a second phase separator having an inlet and at least one outlet having a opening therefrom, said second separator inlet being fluidly connected to said first separator outlet; and a first combustible gas sensor adjacent said second separator outlet, said first sensor being spaced a predetermined distance from said second separator outlet opening.

Another embodiment includes a system for monitoring combustible gas comprising: a first phase separator having at least one outlet; a housing having an inlet and at least one outlet, said housing inlet being connected to said first separator outlet; and a first combustible gas sensor mounted to said first housing, said first sensor having a sensing face being positioned generally perpendicular to said first housing inlet.

Another embodiment for an electrochemical system comprises: an electrochemical cell stack having an oxygen outlet; a first phase separator having an inlet and at least one outlet, said inlet being connected to said cell stack oxygen outlet; a housing having an inlet and at least one outlet, said housing inlet being connected to said first separator outlet; and a first combustible gas sensor mounted to said first housing, said first sensor having a sensing face being positioned generally perpendicular to said first housing inlet.

Another embodiment includes a system for monitoring combustible gas comprising: a gas temperature controller having an inlet and an outlet, said controller reducing the relative humidity of the gas to less than 95% relative humidity; and a combustible gas sensor coupled to said controller outlet.

Another embodiment includes a method for monitoring the level of combustible gas comprising: injecting a gas stream into a housing; impacting said gas stream into a wall; mixing said gas stream with air; and sensing levels of combustible gas in said mixed gas stream.

Another embodiment includes a method for monitoring the level of combustible gas comprising: separating water from a saturated gas stream in a first phase separator; flowing said gas stream through an orifice to restrict flow and decrease pressure of said gas stream; and monitoring the level of combustible gas in said gas stream.

Another embodiment includes a method for monitoring the level of combustible gas comprising: separating water from a saturated gas stream; controlling the temperature of said gas stream to reduce the relative humidity of said gas stream; and monitoring the level of combustible gas in said gas stream.

The above discussed and other features will be appreciated and understood by those skilled in the art from the following detailed description and drawings.

BRIEF DESCRIPTION OF DRAWINGS

Referring now to the drawings, which are meant to be exemplary and not limiting, and wherein like elements are numbered alike:

FIG. 2A is an illustration of the combustible gas sensor shown in FIG. 1;

FIG. 2B is an illustration of an exemplary embodiment of a combustible gas sensor;

FIG. 2C is an illustration of an alternate embodiment of a combustible gas sensor;

FIG. 2D is an illustration of another alternate embodiment of a combustible gas sensor;

DETAILED DESCRIPTION

Figure 1A:
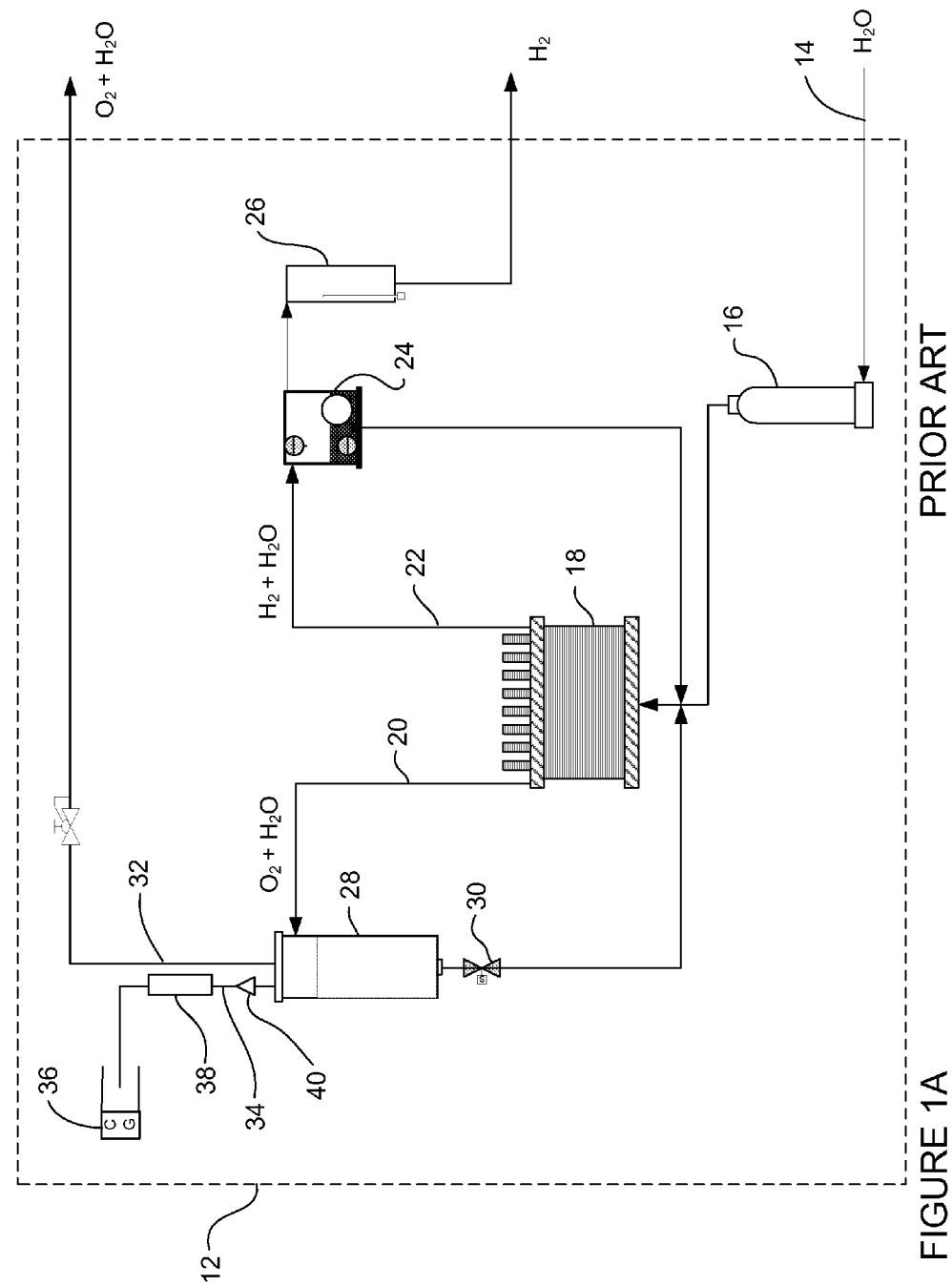
FIG. 1A is a schematic drawing of a electrochemical system having a combustible gas detection system used in the prior art.

Hydrogen gas is a versatile material having many uses in industrial and energy applications ranging from the production of ammonia, to powering vehicles being propelled into space. Since the hydrogen molecule is one of the smallest known particles, containing and controlling leaks of hydrogen gas is very difficult. Monitoring of these leaks is important since it typically is an indicator of performance degradation and or component wear. Typically, prior art systems have used combustible gas sensors to monitor levels of combustible gas in the system. When unacceptable levels of hydrogen are detected in the system, the system is either shut down, or the operator is alerted that preventative maintenance is required.

Commercial combustible gas sensors typically use a technology referred to as a "catalytic bead" type sensor, such as the Detcon, Inc. Model FP-524C. These sensors monitor the percentage of "LEL" or lower explosive limit of combustible gas in a product gas stream. This LEL measurement represents the percentage of a combustible gas (hydrogen, propane, natural gas) in a given volume of air. One limitation of catalytic bead sensors is their sensitivity to moisture in the gas they are monitoring. Once the gas reaches 95% relative humidity, the ability of the sensor to detect combustible gas deteriorates resulting in less than desirable life and reliability performance. Many hydrogen applications, including but not limited to electrochemical cell, electrolyzers, fuel cells, and methane steam reformers, also utilize water in their process which tends to effect the relative humidity of the gas stream. It should be appreciated that while the examples described herein typically refer to electrochemical systems such as electrolyzers or fuel cells, the present invention can be equally applied in any application where a combustible gas needs to be monitored.

Since high relative humidity has undesirable effects, the present invention addresses these issues by three mechanisms: 1) through mixing of the gas stream with dry air, or 2) by controlling the temperature of the gas stream, or 3) by controlling the pressure of the gas stream. Referring to FIGS. 2A–2D, four different combustible gas sensor arrangements are shown. As will be described in more detail herein, these sensor arrangements, either alone, or in combination with other components reduce the relative humidity of the sampled gas to increase the performance of combustible gas measurements.

The combustible gas sensor arrangement utilized by the prior art is shown in FIG. 2A. In this arrangement, the CG sensor device 36 includes a CG sensor 42 and a housing 44. The housing 44 is typically tubular in shape and attaches to the sensor 42 by any convenient means, such as a thread (not shown). The CG sensor 42 also includes a sensing face 43 which detects the levels of combustible gas, this face 43 is located opposite a housing open end 46. A gas sample tube 48 is inserted into the open end 46. During operation, the saturated gas stream 49 exits the sample tube 48 and mixes with the air in the housing allowing some drying of the saturated gas.

An exemplary embodiment of the CG sensor of the present invention is shown in FIG. 2B. In this embodiment, the gas sample tube 48 is positioned a predetermined distance d from the sensor face 43. An air stream 50 is moved through the gap defined by the distance d. During operation, the saturated gas stream 49 exits the sample tube 48 and mixes with the dry air stream 50 drying the gas stream 49 and reducing the relative humidity. When used inside an enclosure, the CG sensor arrangement 51 may additional benefits over the prior art when the air stream 50 is also the main ventilation path as well. This arrangement would allow the sensor arrangement to not only sense hydrogen originating from the phase separator 28, but from elsewhere in the enclosure as well.

An alternate embodiment CG sensor arrangement of the present invention is shown in FIG. 2C. This embodiment 53 is similar to that of FIG. 2A, except that the CG sensor 42 is positioned above the housing 52 and is spaced from the sample tube 48 vertically by a predetermined distance y. The sample tube 48 enters the housing 52 through an opening 54 preferably at an angle generally perpendicular to the sensor face 43. By sizing the distance y appropriately for a given gas flow rate, the sensor can be protected from inadvertent splashing or contamination by water from the gas stream 49. The housing 52 includes an open end 56 opposite the CG sensor 42 to allow drainage of water. During operation, the saturated gas stream 49 enters the housing 52 from the sample tube 48. In the housing, the gas stream mixes with dry air to reduce the relative humidity of the gas being monitored by the sensor 42. Since the sensor 42 is vertically above the sample tube 48, water and oxygen being heavier than air will drain away from the sensor 42 through the opening 56 while the lighter gases, such as hydrogen, will mix with the air and raise to the sensor face 43. By adjusting the distance d' between the end of the sample tube and the housing wall 58, the mixing of the gas stream 49 with the dry air can be enhanced. Openings 55 may be optionally provided in the housing adjacent the sensor 42, or between the housing 52 and the sensor 42 to prevent the buildup of gas resulting in erroneous measurements by the sensor 42.

Another alternate embodiment of the CG sensor arrangement is shown in FIG. 2D. This embodiment 59 is preferable in environments where excessive amounts of water or high levels of relative humidity may be expected. In this embodiment, the sample tube enters a housing 60 and mixes with dry air to reduce the relative humidity. At least one, and preferably several, openings 62 are located vertically above the sample tube 48 and generally opposite a drain opening 66. The openings 62 can either be in the side wall (as shown in FIG. 2D), or in the top of the housing 60. The openings allow the dried gas to disperse into a second housing 64 installed around the first housing 60. The CG sensor 42 is coupled to the second housing 64 and is located generally above the first housing 60. As the dried gas disperses, it enables the sensor 42 to monitor the levels of combustible gas. Optional holes 65 located in the second housing 64 prevent build up of gas in the second housing 64. By arranging the sensor 42 in the second housing, the sensor 42 can be protected from liquid splashing onto the sensor, while minimizing the size of the assembly.

Referring now to FIGS. 3–11, the four CG sensor arrangements 36, 51, 53, 59 are arranged individually and in combination with each other and additional components to provide reduced relative humidity gas streams to the sensor 42.

Figure 1B:
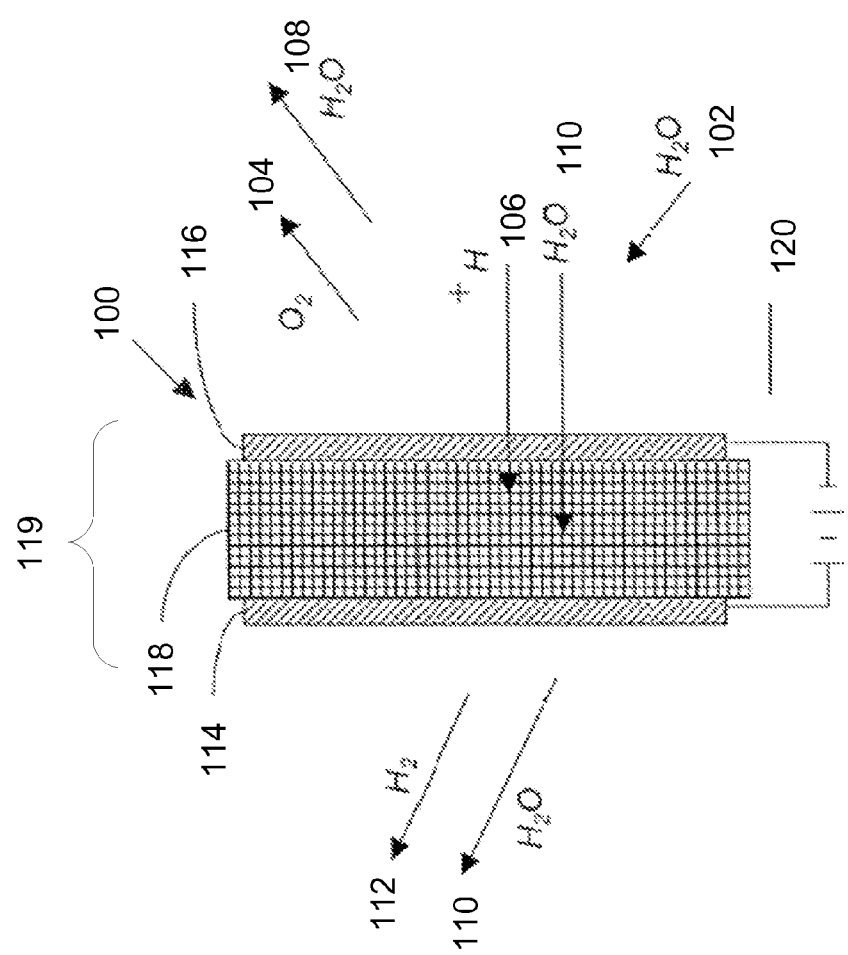
FIG. 1B is a schematic diagram of a partial prior art electrochemical cell showing an electrochemical reaction
Figure 3:
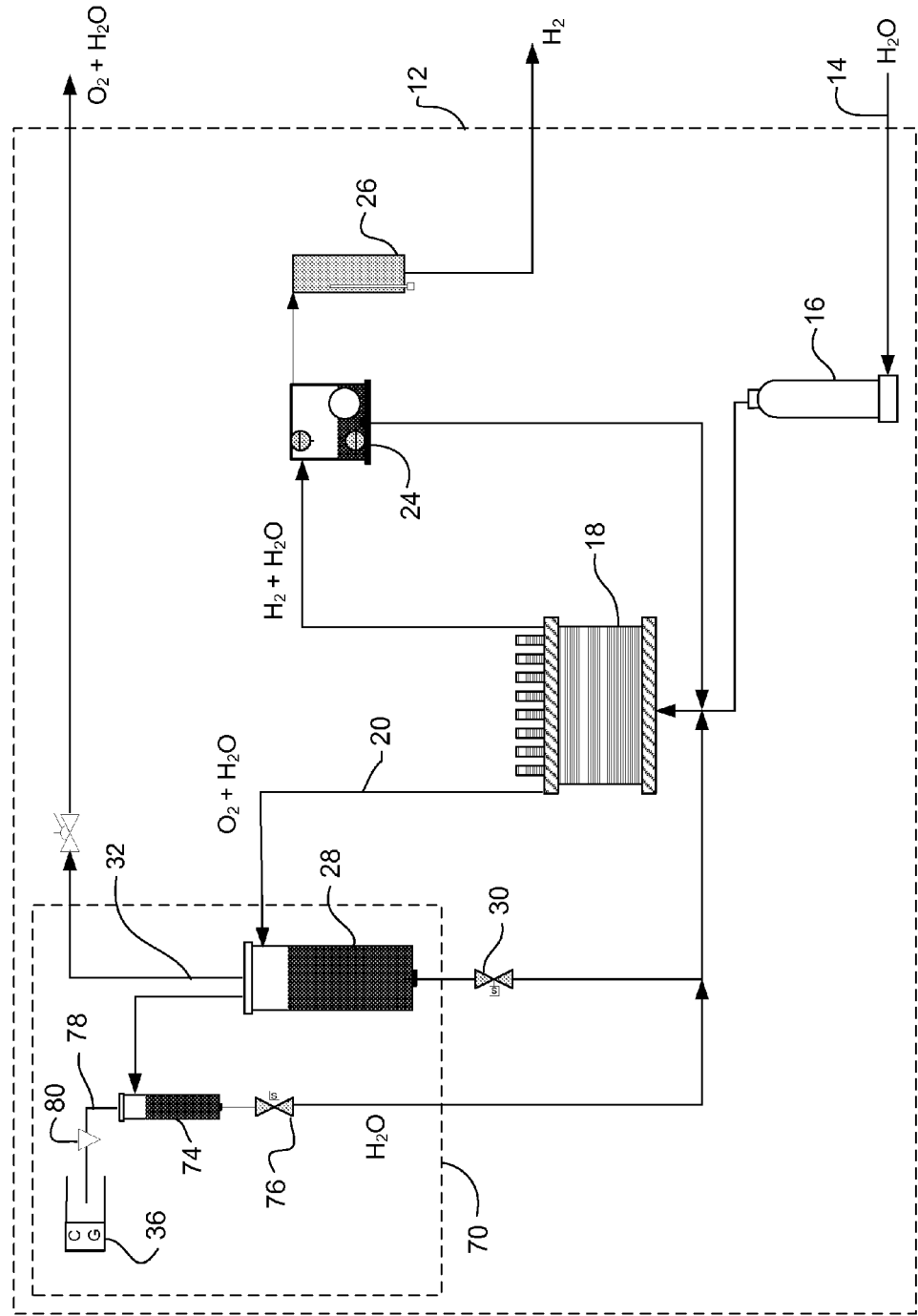
FIG. 3 is a schematic drawing illustrating an exemplary embodiment of a system capable of detecting combustible gas in a vent stream.

Referring to FIG. 3, an electrochemical system 12 of the present invention is shown. Electrochemical cells 18 typically include one or more individual cells arranged in a stack, with the working fluids directed through the cells via input and output conduits formed within the stack structure. The cells within the stack are sequentially arranged, each including a cathode, a proton exchange membrane, and an anode (hereinafter "membrane electrode assembly", or "MEA" 119) as shown in FIG. 1B. Each cell typically further comprises a first flow field in fluid communication with the cathode and a second flow field in fluid communication with the anode. The MEA 119 may be supported on either or both sides by screen packs or bipolar plates disposed within the flow fields, and which may be configured to facilitate membrane hydration and/or fluid movement to and from the MEA 119.

Membrane 118 comprises electrolytes that are preferably solids or gels under the operating conditions of the electrochemical cell. Useful materials include, for example, proton conducting ionomers and ion exchange resins. Useful proton conducting ionomers include complexes comprising an alkali metal salt, alkali earth metal salt, a protonic acid, a protonic acid salt or mixtures comprising one or more of the foregoing complexes. Counter-ions useful in the above salts include halogen ion, perchloric ion, thiocyanate ion, trifluoromethane sulfonic ion, borofluoric ion, and the like. Representative examples of such salts include, but are not limited to, lithium fluoride, sodium iodide, lithium iodide, lithium perchlorate, sodium thiocyanate, lithium trifluoromethane sulfonate, lithium borofluoride, lithium hexafluorophosphate, phosphoric acid, sulfuric acid, trifluoromethane sulfonic acid, and the like. The alkali metal salt, alkali earth metal salt, protonic acid, or protonic acid salt can be complexed with one or more polar polymers such as a polyether, polyester, or polyimide, or with a network or cross-linked polymer containing the above polar polymer as a segment. Useful polyethers include polyoxyalkylenes, such as polyethylene glycol, polyethylene glycol monoether, and polyethylene glycol diether; copolymers of at least one of these polyethers, such as poly(oxyethylene-co-oxypropylene) glycol, poly(oxyethylene-co-oxypropylene) glycol monoether, and poly (oxyethylene-co-oxypropylene) glycol diether; condensation products of ethylenediamine with the above polyoxyalkylenes; and esters, such as phosphoric acid esters, aliphatic carboxylic acid esters or aromatic carboxylic acid esters of the above polyoxyalkylenes. Copolymers of, e.g., polyethylene glycol with dialkylsiloxanes, maleic anhydride, or polyethylene glycol monoethyl ether with methacrylic acid exhibit sufficient ionic conductivity to be useful.

Ion-exchange resins useful as proton conducting materials include hydrocarbon-and fluorocarbon-type resins. Hydrocarbon-type ion-exchange resins include phenolic resins, condensation resins such as phenol-formaldehyde, polystyrene, styrene-divinyl benzene copolymers, styrene-butadiene copolymers, styrene-divinylbenzene-vinylchloride terpolymers, and the like, that can be imbued with cation-exchange ability by sulfonation, or can be imbued with anion-exchange ability by chloromethylation followed by conversion to the corresponding quaternary amine.

Fluorocarbon-type ion-exchange resins can include, for example, hydrates of tetrafluoroethylene-perfluorosulfonyl ethoxyvinyl ether or tetrafluoroethylene-hydroxylated (perfluoro vinyl ether) copolymers and the like. When oxidation and/or acid resistance is desirable, for instance, at the cathode of a fuel cell, fluorocarbon-type resins having sulfonic, carboxylic and/or phosphoric acid functionality are preferred. Fluorocarbon-type resins typically exhibit excellent resistance to oxidation by halogen, strong acids, and bases. One family of fluorocarbon-type resins having sulfonic acid group functionality is NAFION™ resins (commercially available from E. I. du Pont de Nemours and Company, Wilmington, Del).

Electrodes 114 and 116 comprise catalysts suitable for performing the needed electrochemical reaction (i.e., electrolyzing water to produce hydrogen and oxygen). Suitable electrodes comprise, but are not limited to, platinum, palladium, rhodium, carbon, gold, tantalum, tungsten, ruthenium, iridium, osmium, and the like, as well as alloys and combinations comprising one or more of the foregoing materials. Electrodes 114 and 116 can be formed on membrane 118, or may be layered adjacent to, but in contact with or in ionic communication with, membrane 118.

Flow field members (not shown) and support membrane 118, allow the passage system fluids, and preferably are electrically conductive, and may be, for example, screen packs or bipolar plates. The screen packs include one or more layers of perforated sheets or a woven mesh formed from metal or strands. These screens typically comprise metals, for example, niobium, zirconium, tantalum, titanium, carbon steel, stainless steel, nickel, cobalt, and the like, as well as alloys and combinations comprising one or more of the foregoing metals. Bipolar plates are commonly porous structures comprising fibrous carbon or fibrous carbon impregnated with polytetrafluoroethylene or PTFE (commercially available under the trade name TEFLON® from E. I. du Pont de Nemours and Company).

After hydrogen and oxygen have been disassociated from the water, the hydrogen exits the electrochemical cell 18 as described herein above via the separator 24 and an optional dryer 26. The oxygen gas and excess water exit the electrochemical cell through a conduit 20 which carries the oxygen and water into a phase separation and gas monitoring subsystem 70.

As the oxygen/water stream enters the phase separator 28 the stream experiences a slight pressure drop causing some of the water entranced in the stream to condense and drop to the bottom of the phase separator. The separated oxygen gas stream exits the phase separator 28 via a conduit 32 and exits the system 12. It should be noted that while the phase separator 28 removes water from the gas stream, the oxygen gas typically exits the separator 28 in a saturated condition with a relative humidity in excess of 95%.

In the exemplary embodiment shown in FIG. 3, a sample conduit 72 connects the phase separator 28 with a second phase separator 74. As the gas stream enters the second separator 74, additional water is removed from the gas. An optional solenoid valve 76 is connected to the phase separator 74 to allow periodic draining of water for disposal, or recycling back into the electrochemical cell 18 feed loop. The separated gas in second separator 74 exits through a conduit 78, passing through an orifice 80 which reduces the pressure of the gas and restricts the flow of gas into the combustible gas sensor 36. The size of the orifice 80 will depend on the application, and the amount of flow restriction desired. In general, the smallest orifice that provides a minimal risk of becoming plugged is desired. In the exemplary embodiment, the preferred orifice 80 has an opening size of less and 0.025 inches, and more preferably has an opening size of less than 0.016 inches. It should be appreciated that while the phase separator 74 is illustrated as a standard phase separation device (long tubular vessel, mounted vertically), this device may also be a coalescing filter which is periodically replaced. The drop in pressure due to the orifice 80 lowers the relative humidity from near 100% when the gas enters the second separator 74 to less than 80%.

Figure 4:
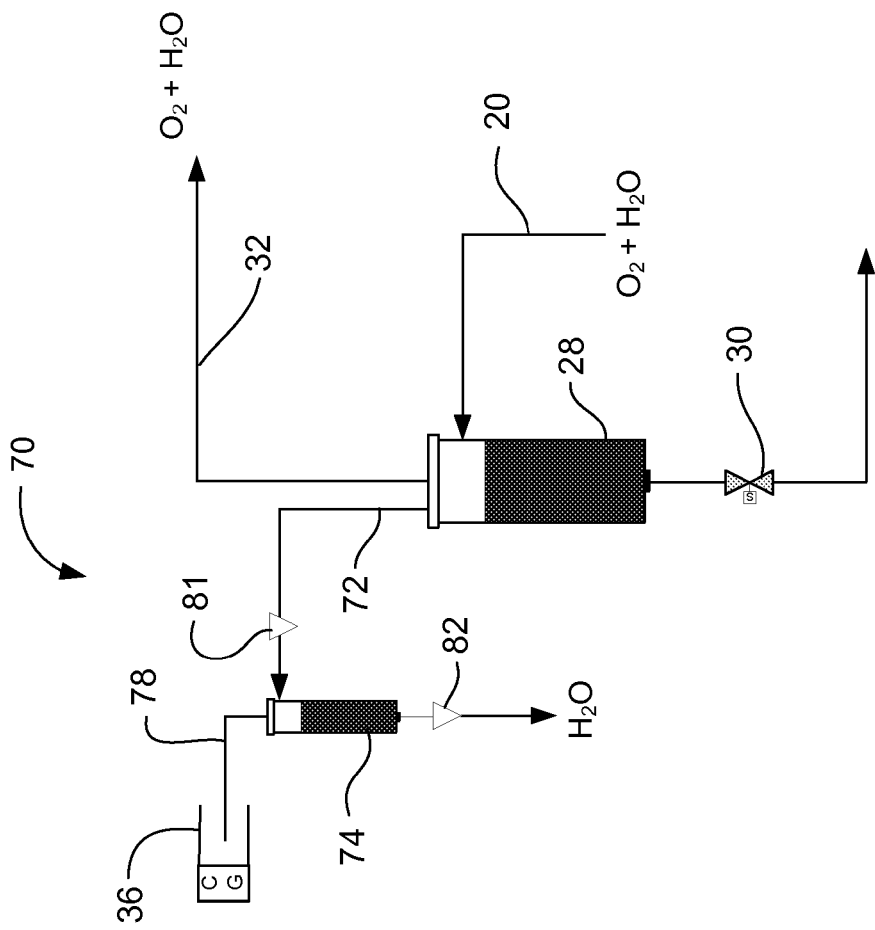
FIGS. 4–11 are a schematic drawings illustrating an alternate embodiments of a system capable of detecting combustible gas in a vent stream.

An alternate embodiment of the phase separation and gas monitoring system 70 is shown in FIG. 4. In this embodiment, the gas leaving separator 28, passes through an orifice 81, which drops the pressure and restricts the flow of gas into a second separator 74. Preferably, the orifice 81 has an opening size of less than 0.025 inches, and more preferably has an opening size of less than 0.016 inches. In this configuration, since the gas in the second phase separator 74 is at a lower pressure, the second separator 74 can be drained using an orifice 82 which provides sufficient flow to prevent the second separator 74 from over-filling with water. The gas stream from the second separator 74 moves to the combustible gas sensor 36 via conduit 78. The drop in pressure due to the orifice 81 and second separator 74 lowers the relative humidity from near 100% when the gas leaves the separator 28 to less than 95% when it reaches the combustible gas sensor.

Figure 5:
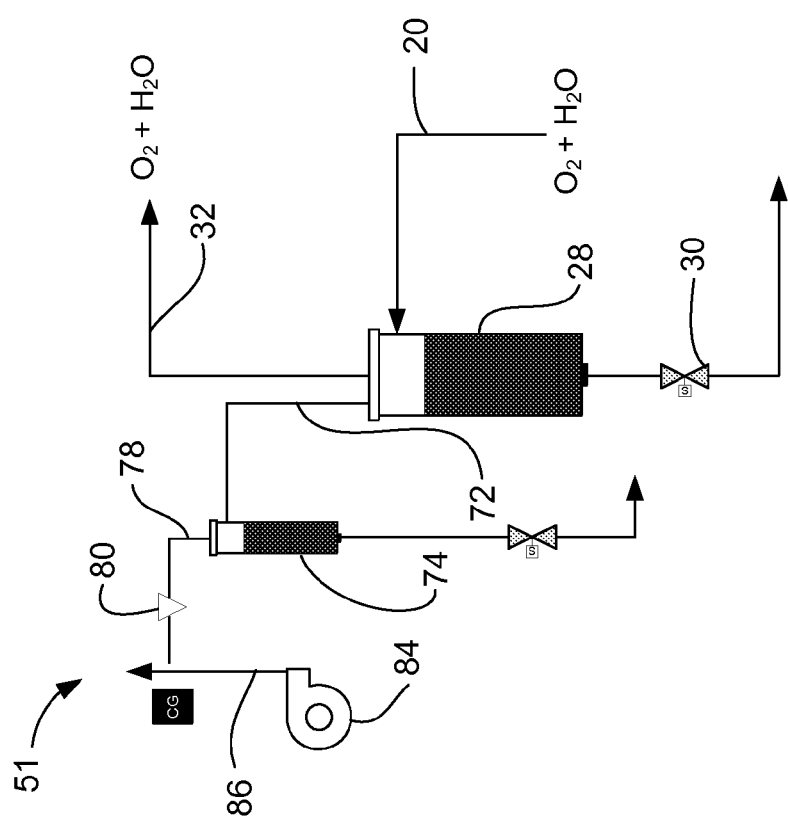

Another alternate embodiment of the phase separation and gas monitoring system 70 is shown in FIG. 5. In this embodiment, the gas leaving second separator 74 through conduit 78, passes through an orifice 80, which drops the pressure and restricts the flow of gas to the CG sensor arrangement 51. As the gas stream leaves the conduit 78, it passes through a stream of dry air 86 which further reduces the relative humidity of the gas stream as it reaches the CG sensor 42. A fan 84 either coupled to the combustible gas sensor arrangement 51 or elsewhere in the system 12, provides the mechanism for creating dry air stream 86.

Figure 6:
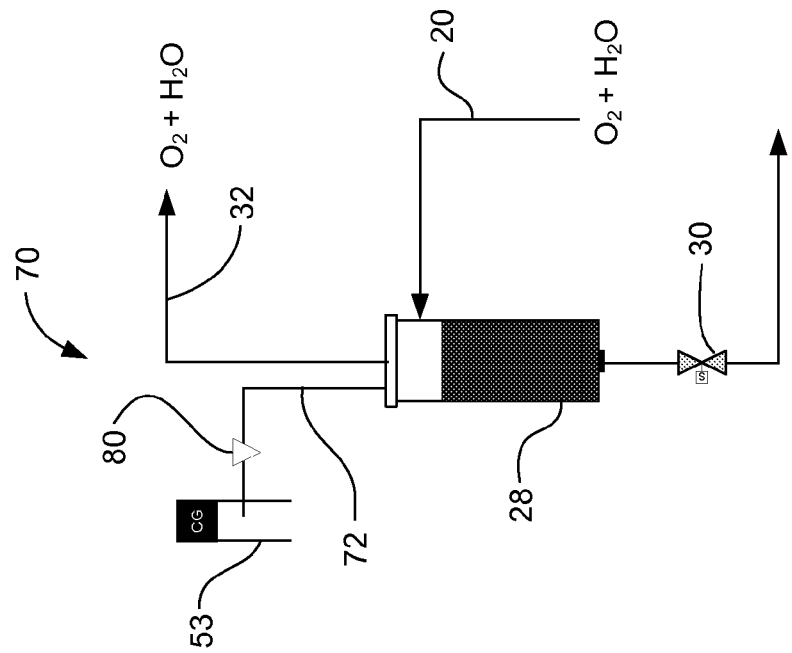

Another alternate embodiment of the phase separation and gas monitoring system 70 is shown in FIG. 6. This embodiment uses the CG sensor arrangement 53 in combination with an orifice 80 connected to a conduit 72 which carries the gas stream from the separator 28. As described herein above, as the gas stream enters the sensor arrangement 53, the gas stream impacts on the housing wall enhancing the mixing of the gas stream with dry air allowing for improved detection of combustible gasses.

Figure 8:
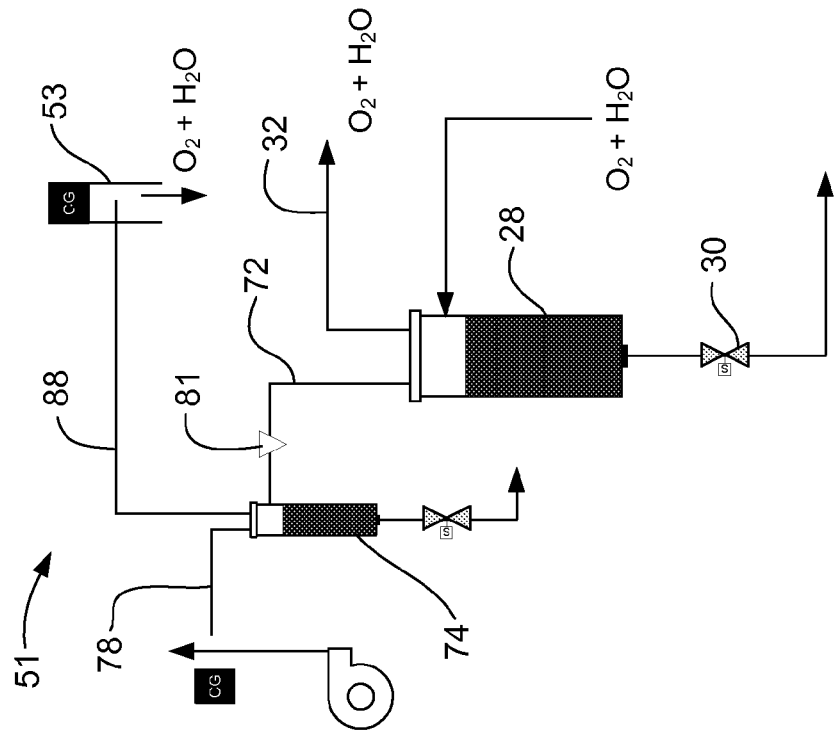
Figure 7:
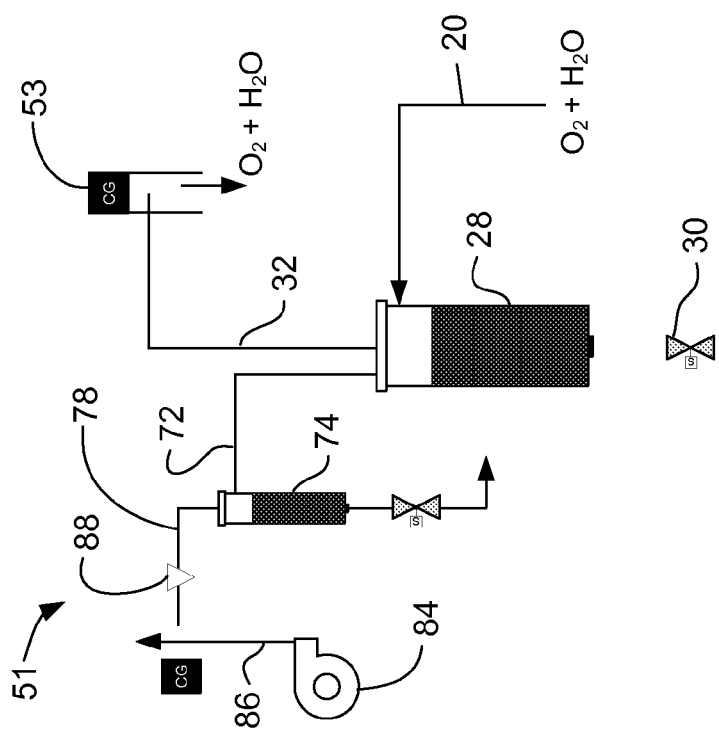

FIG. 7 and FIG. 8 provide yet other embodiments utilizing redundant sensors to detect the presence of combustible gas in the gas stream. In addition to improving reliability in monitoring capability, each of these embodiments utilize a different CG sensor arrangement which increases the reliability further by lowering the risk that an environmental factor (air pressure, temperature, humidity and the like) will effect both sensors simultaneously. It should be appreciated that the specific CG sensor arrangements used in the embodiments shown in FIGS. 7–8 are examples, and that any combination of CG sensor arrangements described herein could be utilized to achieve the same effect.

In the alternate embodiment shown in FIG. 7, the first sensing arrangement 53 monitors the main gas stream that exits separator 28 through conduit 32. The gas stream enters the CG sensor arrangement 53 where it mixes with dry air to provide monitoring capability as described herein above. The gas stream exits the CG sensor arrangement 53 through opening 56 (FIG. 2C) and vents to the atmosphere. It should be appreciated the CG sensor arrangement 53 could be positioned internally, or externally to the system 12. A second CG sensor arrangement 51 is provided through sampling conduit 72 which provides a gas stream from the phase separator 28 to a second phase separator 74 which provides further reduction in the gas stream's water content. The gas stream exits the phase separator 74 through conduit 78, passes through an orifice 80, and is monitored by sensor arrangement 51. As described herein above, the gas stream mixes with a dry air stream 86 which provides further reduction in the relative humidity and improvement in monitoring performance.

The alternate embodiment in FIG. 8 is arranged to also provide redundant monitoring of a sample stream. In some applications, this may provide additional benefits over the embodiment illustrated in FIG. 7 in that the primary vent stream is not interrupted. In this embodiment, a sample conduit 72 allows the gas stream to move from the separator 28 to a second separator 74 through an orifice 81 which lowers the pressure and restricts the flow of the gas stream. In the second separator 74, additional water is removed and the gas stream exits through both conduit 78, that delivers the gas stream to CG sensor arrangement 51, and through conduit 88 to the CG sensor arrangement 53. It should be appreciated that similar to the embodiment in FIG. 5, the orifice 81 may be positioned after the second separator 74. Additionally, instead of having two conduits exit the second separator 74, a single conduit may be used with the conduits 78, 88 branching off from the single conduit to the respective CG sensor arrangements 51, 53.

Figure 10:
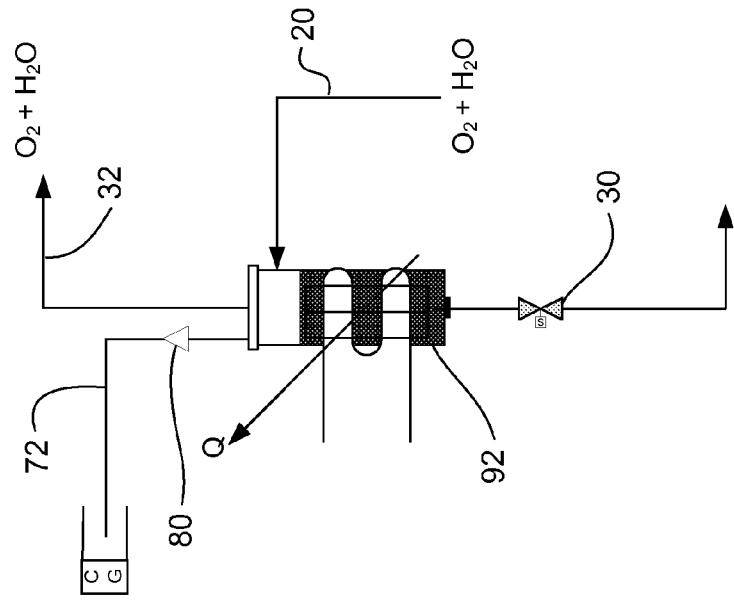
Figure 9:
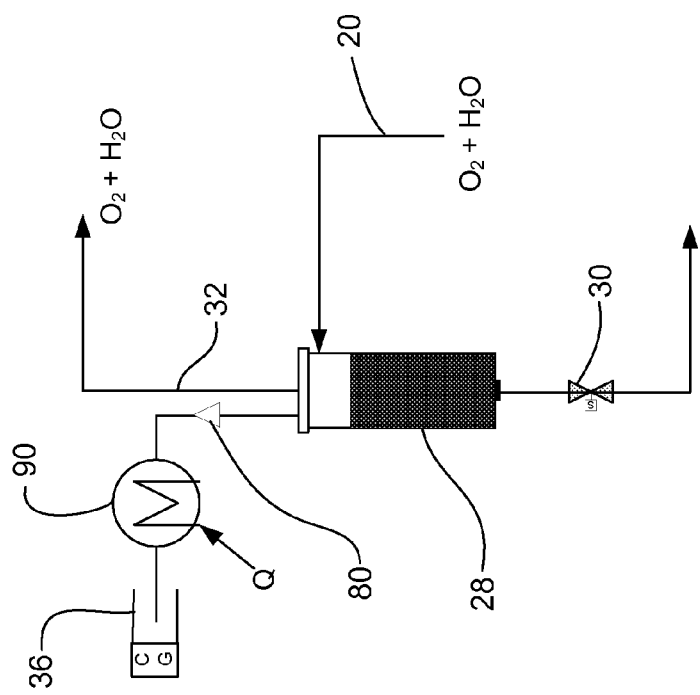
Figure 11:
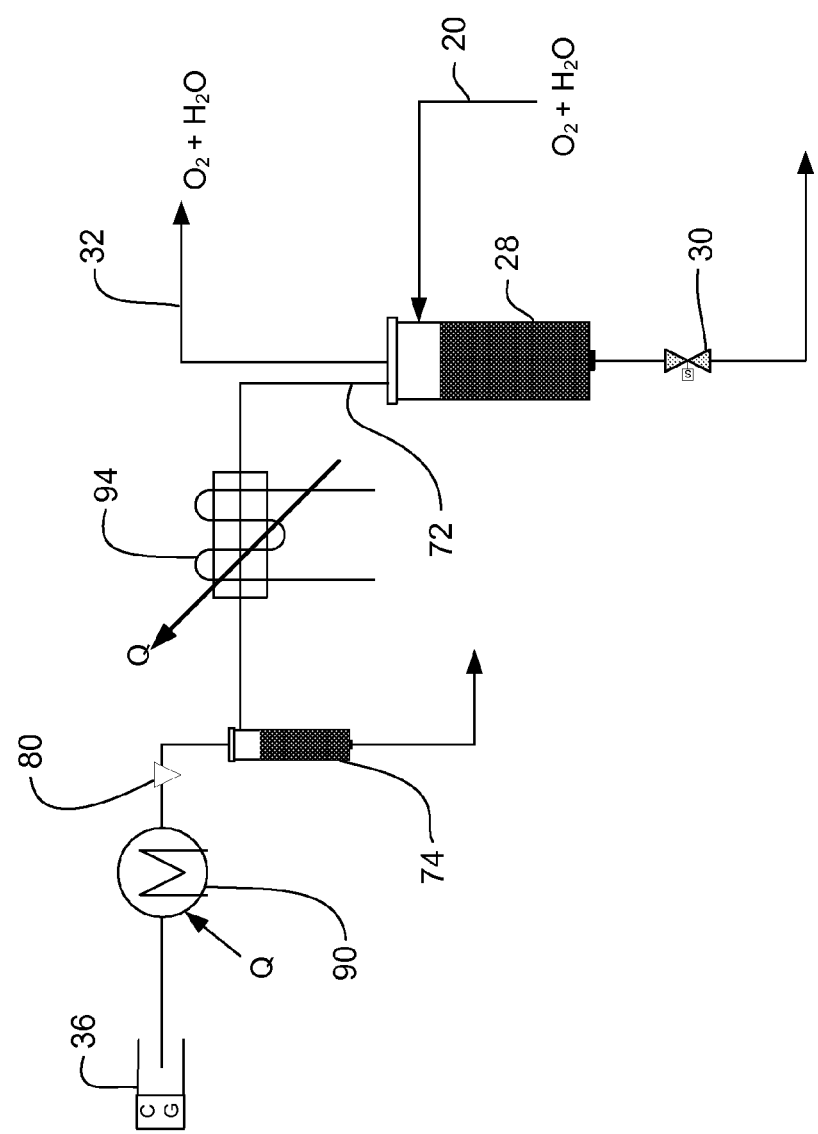

FIGS. 9–11 illustrate alternate embodiments utilizing temperature control as a means for reducing the relative humidity of the gas stream. A gas has a given relative humidity level depending on the temperature and pressure of the gas. Since the pressure of the system 12 will be generally known for a given application, by adjusting the temperature of the gas stream, the relative humidity of the monitored gas can be lowered to the operating range of the sensor.

The exemplary embodiment utilizing temperature control is shown in FIG. 9. Saturated gas from the system 12 enters a phase separator 28 where most of the water entrained in the gas stream is separated and recycled back into the system through valve arrangement 30. A saturated gas stream exits the phase separator 28 and travels via conduit 72 through an orifice 80 which lowers the pressure and restricts the flow of the gas stream. A heat exchanger 90 raises the temperature of the gas to a sufficient level to lower the relative humidity to less than 95%. The gas exits the conduit 72 into the CG sensor arrangement 36. The type of heat exchanger used can be of any suitable type, including but not limited to cross-flow, counter-flow or parallel-flow exchangers, or resistive heat elements such as heat tape. Additionally, any of the CG sensor arrangements described herein may be used in this arrangement and additional phase separation devices may be utilized as needed for a particular application.

An alternate embodiment shown in FIG. 10 uses the cooling of the gas stream to condense additional water from the gas stream and thus lower the relative humidity. In this embodiment, a gas stream enters the phase separator 92 from conduit 20. The phase separator 92 is cooled by a suitable device, including but not limited to thermoelectric cooling devices, to cause water vapor in the gas stream to condense and be captured within the phase separator 92. The condensed water is removed from the separator 92 via valve arrangement 30 and either recycled, or similarly disposed of. The gas stream exits the phase separator 92 via conduit 72 through an orifice 80 which lowers the pressure and restricts the flow of the gas stream. The gas exits the conduit 72 into the CG sensor arrangement 36. While the embodiment illustrated in FIG. 10 shows the cooling device coupled with a single or primary phase separator, other arrangements would be equally effective including the addition and cooling of a second subsequent phase separator. Depending on the application, the cooling of a second phase separation may be preferable since it may reduce the amount of cooling necessary to achieve the desired final relative humidity. Additionally, while the CG sensor arrangement 36 is illustrated, any of the CG sensor arrangements 51, 53, 59 described herein may be used in this arrangement.

Another alternate embodiment utilizing both heating and cooling to lower the relative humidity is shown in FIG. 11. In this embodiment, a gas stream enters the phase separator 28 where entrapped water in the gas stream is separated. A sample gas stream 72 is cooled by a suitable cooling device 94 to condense additional water from the saturated gas stream. A second phase separator 74 separates the condensed water and drains it away for disposal or recycling. The gas stream then leaves the second separator 74 passing through an orifice 80 that restricts the gas flow and further drops the pressure of the gas stream. A heater 90 then heats the gas stream further reducing the relative humidity of the gas stream prior to monitoring by the CG sensor arrangement 36. It should be appreciated that the heater device 90 and cooling device 94 can be any suitable device, including but not limited to the heating and cooling devices described herein above.

While preferred embodiments have been shown and described, various modifications and substitutions may be made thereto without departing from the spirit and scope of the invention. For example, while the embodiments shown referred specifically to an electrochemical system generating hydrogen, this invention would apply equally to any system where there is a potential for mixing hydrogen with air or oxygen including, but not limited to photolysis, fuel cells, steam methane reformers or hydrocarbon reformers. Accordingly, it is to be understood that the present invention has been described by way of illustrations and not limitation.

The invention claimed is:

1. A system for monitoring combustible gas comprising:
   a first phase separator having an inlet for receiving a two phase gas-water mixture, and a first outlet;
   a second phase separator having an inlet for receiving a portion of said two phase gas-water mixture, a first outlet having a opening therefrom, a second outlet for draining water, wherein said second phase separator inlet is fluidly connected to said first phase separator outlet to provide a conduit for transferring said portion of said gas-water mixture from said first phase separator to said second phase separator; and
   a first combustible gas sensor adjacent said second phase separator first outlet, said first sensor being spaced a predetermined distance from said second phase separator first outlet opening.

2. The system for monitoring combustible gas of claim 1 further comprising an air movement device, said device arranged to move air between said second phase separator first outlet opening and said first combustible gas sensor.

3. The system for monitoring combustible gas of claim 2 wherein said first sensor includes a sensing surface, said sensor being arranged such that said sensing surface is perpendicular to said second phase separator first outlet opening.

4. The system for monitoring combustible gas of claim 3 wherein said air movement device is arranged to move air in a direction parallel to said sensing surface.

5. The system of claim 2 wherein said second phase separator outlet opening is separated from said second phase separator by a conduit.

6. The system of claim 5 further comprising an orifice coupled to said conduit, said orifice being arranged between said second phase separator and said first outlet opening.

7. The system of claim 6 wherein said second phase separator includes a valve, said valve arranged to drain water from said second phase separator second outlet.

8. The system of claim 7 wherein said orifice has an opening of less than 0.025 inches.

9. The system of claim 2 wherein said second phase separator is a coalescing filter.

* * * * *